(12) United States Patent
Aime et al.

(10) Patent No.: US 8,945,512 B2
(45) Date of Patent: Feb. 3, 2015

(54) ADDUCTS BETWEEN MAGNETIC RESONANCE SHIFT REAGENTS AND SUBSTRATES CONTAINING EXCHANGEABLE PROTONS FOR "CEST" APPLICATIONS

(75) Inventors: Silvio Aime, Milan (IT); Enzo Terreno, Milan (IT); Daniela Delli Castelli, Milan (IT); Giovanni Battista Giovenzana, Milan (IT)

(73) Assignee: Bracco Imaging SpA, Milan (IT)

( * ) Notice: Subject to any disclaimer, the term of this patent is extended or adjusted under 35 U.S.C. 154(b) by 2768 days.

(21) Appl. No.: 10/552,851

(22) PCT Filed: Apr. 6, 2004

(86) PCT No.: PCT/EP2004/003684
§ 371 (c)(1),
(2), (4) Date: Jul. 21, 2006

(87) PCT Pub. No.: WO2004/089424
PCT Pub. Date: Oct. 21, 2004

(65) Prior Publication Data
US 2007/0036727 A1    Feb. 15, 2007

(30) Foreign Application Priority Data
Apr. 11, 2003  (EP) .................................. 03008456

(51) Int. Cl.
| A61B 5/055 | (2006.01) |
| A61B 5/00 | (2006.01) |
| C07K 1/00 | (2006.01) |
| C08B 37/00 | (2006.01) |
| A61K 49/08 | (2006.01) |
| A61K 49/10 | (2006.01) |
| A61K 49/14 | (2006.01) |

(52) U.S. Cl.
CPC ............... *A61K 49/085* (2013.01); *A61K 49/10* (2013.01); *A61K 49/146* (2013.01)
USPC .................... 424/9.32; 424/9.321; 424/9.363; 530/400; 536/53

(58) Field of Classification Search
None
See application file for complete search history.

(56) References Cited

U.S. PATENT DOCUMENTS 5,271,924 A    12/1993    Hashiguchi et al.

FOREIGN PATENT DOCUMENTS

| EP | 1106186 | 6/2001 |
| EP | 1331012 | 7/2003 |
| WO | WO 92/13572 | 8/1992 |
| WO | WO 96/38184 | 12/1996 |
| WO | WO 99/55230 | 11/1999 |
| WO | WO 00/66180 | 11/2000 |
| WO | WO 0066180 A1 * | 11/2000 |
| WO | WO 02/40060 | 5/2002 |
| WO | WO 02/43775 | 6/2002 |
| WO | WO 03/013617 | 2/2003 |

OTHER PUBLICATIONS

Aime, et al., "Paramagnetic Lanthanide(III) Complexes as Ph-sensitive Chemical Exchange Saturation Transfer (CEST) Contrast Agents for MRI Application", 2002, Magnetic Resonance in Medicine, 47(4), pp. 639-648.*
Aime, S., et al. "Paramagnetic Lanthanide(III) complexes as pH-sensitive Chemical Exxchange Saturation Transfer (CEST) COntrast Agents for MRI Applications", 2002, Magnetic Resonance in Medicine, 47, pp. 639-648.*
Aime, S., et al., "Molecular Recognition of R- and T-states of Human Adult Hemoglobin by Paramagnetic Gd(III) Complex by Means of the Measurement of Solvent Water Proton Relaxation Rate", 1995, JACS, 117, pp. 9365-9366.*
Frullano, L. et al., "Structures in MRI COntrast Agents", 2002, Topics in Current Chemistry, 221, pp. 25-60.*
PCT International Search Report and Written Opinion for PCT/EP04/03684 dated Sep. 10, 2004.
Zhang, S. et al., "A Novel Ph-Sensitive MRI Contrast Agent", *Angewandte Chemie*, vol. 38, No. 21, Nov. 2, 1999, pp. 3192-3194.
Aime et al., "Parmagnetic Lanthanide (III) Complexes as Ph-Sensitive Chemical Exchange Saturation Transfer (CEST) Contrast Agents for MRI Application", *Magnetic Resonance in Medicine*, vol. 47, No. 4, 2002, pp. 639-648.
Aime et al., "Non-covalent conjugates between cationic polyamino acis and GdIII chelates: a route for seeking accumulation of MRI-contrast agents at tumor targeting sites" *Chemistry*, vol. 6, No. 14, Jul. 2000, pp. 2609-2617.
Allen et al., "Synthesis and visualization of a membrane-permeable MRI contrast agent" *JBIC*, vol. 8. No. 7, Sep. 2003, pp. 746-750.
Allen et al, "Cellular delivery of MRI contrast agents" *Chemistry and Biology*, vol. 11, No. 3, Mar. 2004, pp. 301-307.

* cited by examiner

*Primary Examiner* — Michael G Hartley
*Assistant Examiner* — Lance Rider
(74) *Attorney, Agent, or Firm* — Robert E. Alderson, Jr.

(57) ABSTRACT

Disclosed are CEST paramagnetic agents comprising a substrate (SH) containing mobile protons bonded to a paramagnetic chelate (SR) containing a metal selected from iron (11) (high-spin configuration), iron (111), cobalt (11), rhodium (11), copper (11), nickel (11), cerium (111), praseodymium (111), neodymium (111), dysprosium (111), erbium (111), terbium (111), holmium (111), thulium (III), ytterbium (III) and europium (111).

5 Claims, 14 Drawing Sheets

ADDUCTS BETWEEN MAGNETIC RESONANCE SHIFT REAGENTS AND SUBSTRATES CONTAINING EXCHANGEABLE PROTONS FOR "CEST" APPLICATIONS

This application is the national stage filing of corresponding international application number PCT/EP2004/003684, filed Apr. 6, 2004, which claims priority to and the benefit of European Application No. 03008456.0, filed Apr. 11, 2003, all of which hereby incorporated by reference.

The present invention relates to paramagnetic adducts useful in Magnetic Resonance Imaging (MRI) procedures which use saturation transfer to create image contrast.

BACKGROUND TO THE INVENTION

The generation of contrast in an MRI image through irradiation of mobile protons in the tissues has already been reported in U.S. Pat. No. 5,050,609. The use of exogenous contrast agents (originally called CEDST agents, and now called CEST agents) containing at least one mobile proton in exchange with water was disclosed in WO 00/66180. That document does not expressly refer to the possibility of using paramagnetic complexes as CEST agents. The preferred compounds are diamagnetic molecules such as sugars, aminoacids, heterocyclic compounds, nucleosides, imidazoles and derivatives, guanidine, etc.

The same document also claims methods for in vitro and in vivo determination of the pH, temperature and metabolite concentration by administering a contrast agent having two sets of magnetically non-equivalent mobile protons. Selective irradiation of the two pools and application of a ratiometric method allows a transfer effect to be measured independently of the concentration of contrast medium. Saturation transfer implies that the mobile protons of the CEST agent do not coalesce with the bulk water, which means that the separation between the resonance frequencies of the two sets of mobile protons must be greater than the exchange rate. Moreover, the extent of the transfer is directly proportional to the exchange rate of the protons of the agent, which means that an increase in separation of the resonance frequencies of the two exchanging signals increases the efficiency of saturation transfer. The use of CEST paramagnetic contrast agents was therefore considered in WO 02/43775, which claims the use of paramagnetic complexes having mobile protons whose saturation transfer (which is better than that of the diamagnetic compounds exemplified in U.S. Pat. No. 5,050,609) can be sensitive to parameters of diagnostic interest such as pH, temperature, metabolite concentration, etc.

However, the possibility of using as CEST agents systems constituted by non-covalent adducts formed by a substrate having protons in exchange with bulk water (including types similar to those exemplified in U.S. Pat. No. 5,050,609) and by a paramagnetic complex able to increase the separation of their resonance frequencies off the bulk water is not considered in the above-mentioned documents or in the literature. With this approach, the paramagnetic agent will be chosen on the basis of its Shift Reagent (SR) characteristics in relation to the properties of the compound containing the exchangeable protons.

SUMMARY OF THE INVENTION

The present invention relates to the preparation and use of paramagnetic CEST agents wherein the chemical shift of the mobile protons which must be irradiated to observe saturation transfer has been suitably "shifted" as a result of interaction of the substrate with a paramagnetic chelate containing a metal selected from iron (II) (high-spin configuration), iron (III), cobalt (II), rhodium (II), copper (II), nickel (II), cerium (III), praseodymium (III), neodymium (III), dysprosium (III), erbium (III), terbium (III), holmium (III), thulium (III), ytterbium (III) and europium (III). The mobile protons can belong to diamagnetic or paramagnetic substrates, provided that in the latter case their chemical shift is influenced by non-covalent interaction with the paramagnetic species.

The first aspect of the invention consequently relates to paramagnetic CEST agents constituted by diamagnetic substrates containing mobile protons (SH units) bonded by means of electrostatic interactions or covalent bonds to paramagnetic chelates (SR units) which interact reversibly with the substrates.

The invention also relates to diagnostic compositions containing CEST agents as defined above, mixed with a suitable vehicle.

All the molecules already described in U.S. Pat. No. 5,050,609 and WO 00/66180 can be used as molecules with mobile protons, with particular preference for linear and macrocyclic polyamines such as cyclen (1,4,7,10-tetraazacyclododecane), polyaminoacids such as polyarginine, proteins such as human serum albumin, polysaccharides, polycyclodextrins, synthetic polymers (polyamidoamines, peramidated polyaminoacids, and dendrimers containing amide groups). Cyclen, polyarginine and albumin are particularly preferred.

Exchangeable protons may also belong to water molecules which, following interaction with the SH substrate and due to the nature of the adduct [(SR)(SH)], are "shifted" from the bulk water signal and are in suitable exchange conditions with it. This category of SH substances includes polysaccharide systems, especially systems which form supramolecular aggregates able to trap molecules of water and SR units. A further extension of this concept includes any system wherein SR and water molecules are trapped in the same compartment, and at the same time the water molecules (whose chemical shift is influenced by the SR unit) are in suitable exchange conditions with the bulk water. A non-exhaustive list of systems which can be used to obtain this compartmentalisation includes liposomes, nano- and micro-vesicular systems, protein cavities and cells.

The adducts according to the invention can be prepared by simple mixing of molecules having mobile protons with paramagnetic chelates, in suitable molar ratios which depend on the affinity between the substrate and the SR unit:

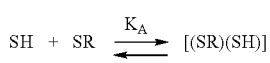

$$SH + SR \xrightleftharpoons{K_A} [(SR)(SH)]$$

This affinity can be expressed by the value of the thermodynamic constant of association ($K_A$), which must be greater than 10. The adducts can then be isolated and purified by chromatographic techniques and/or freeze-drying, precipitation, evaporation and the like.

DETAILED DESCRIPTION

Figure 1:
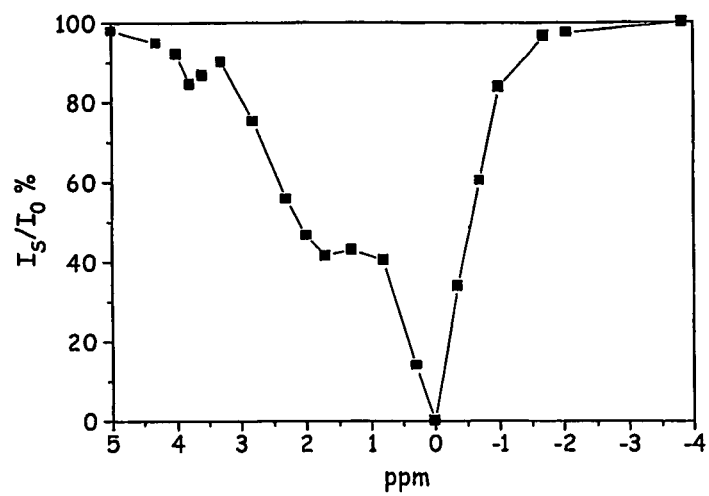
FIG. 1 illustrates the intensity of the NMR signal of the bulk water according to the irradiated frequency, expressed in ppm in relation to the water.

According to a first embodiment of the invention, the SR unit possesses chemical characteristics able to recognise the portion of the substrate molecule containing the mobile protons so as to significantly influence their chemical shift. For example, in the case of adducts between [LnDOTP]$^{4-}$ (Ln is a lanthanide) and the preferred substrates cyclen, polyarginine and HSA, the interaction takes place through electrostatic bonds.

Other examples relating to the electrostatic interaction between substrate and SR unit are those in which the [LnDOTP]$^{4-}$ is able to influence the chemical shift value of the mobile protons of diamagnetic molecules such as Co(III)-sarcophagine, Co(III)-(ethylenediamine)$_3$ and agmatine.

Recognition of the substrate-SR unit can also take place through hydrophobic (e.g. in the case of polycyclodextrins) or mixed interactions (e.g. in the case of proteins).

Alternatively, the SR unit can be trapped in polymer systems with high biocompatibility such as hydrogels or crosslinked proteins in which it can perform its effect towards the slow-exchange water molecules present in those systems.

Other systems of interest are those wherein differentiation between the pools of exchangeable protons takes place as a result of the effects of compartmentalisation.

According to this embodiment of the invention, the SR unit and SH substrate can be compartmentalised in suitable biocompatible systems such as liposomes, nanoparticles, microemulsions and protein cavities (e.g. apoferritin), in which water (unlike the SR unit and the substrate) can be freely exchanged between the inside and outside of the compartment. In this way, the effect of the SR unit could also be performed by means of a simple variation in magnetic susceptibility able to influence the resonance frequency of the mobile protons of the substrate in the compartment without requiring their interaction, with the advantage of making the irradiation frequency of the mobile protons of the substrate almost constant.

If the SH-SR agent is compartmentalised in a system wherein the exchange rate of water between the inside and the outside of the compartment is very slow, and the quantity of water in the compartment containing the unit is sufficient to observe it in the MR image, the effect of saturation transfer could be considerably increased due to the increase in the local concentration of SR and in the substrate containing the mobile protons.

Alternatively, the shift agent could be chosen in order to influence resonance of the bulk water signal only. This effect would in any event increase the separation of the resonance frequencies between water and substrate, thus allowing irradiation of the mobile protons of the substrate. An example of this kind, unrelated to CEST, is reported by Otting et al. (J. Am. Chem. Soc., 1991, 113, 4363), who used Co(II) to "shift" the bulk water signal, thus allowing observation of the water molecules trapped in a site of protein BPTI, which the shift agent is unable to enter.

The SR unit and the SH unit can also be conjugated through a covalent bond so as to guarantee the same biodistribution of the two units in vivo. In this case, the effect of the SR unit is not performed intramolecularly towards the protons of the SH unit, but intermolecularly, through a mechanism of self-identification/self-aggregation.

A preferred compound in this category is the following:

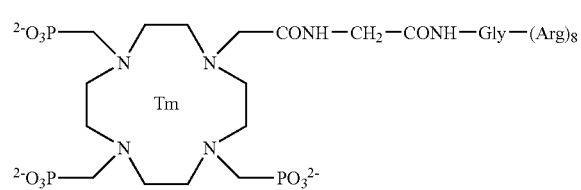

wherein intermolecular self-identification takes place between a negatively charged SR unit of one molecule and the positive polyarginine chain of another. In this compound, the choice of the number of arginine residues on the side chain was dictated partly by the fact that the structural motif (Arg)$_8$, reminiscent of the peptide fragment 48-60 of virus HIV-1, is known for its ability to be recognised and internalised by the cells (Suzuki et al., J. Biol. Chem., 2002, 277, 2437).

This compound can be prepared according to the following synthesis chart:
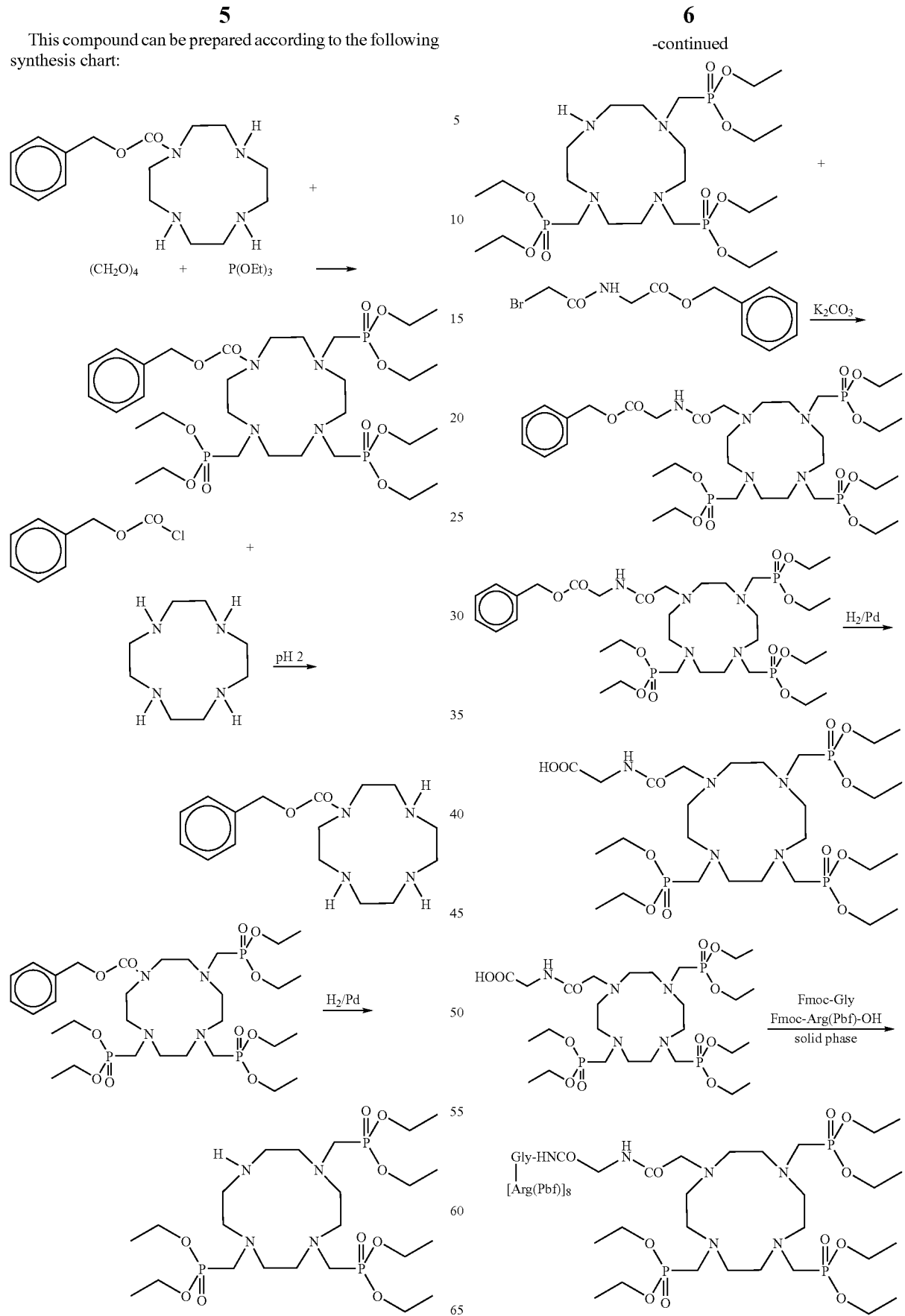

-continued

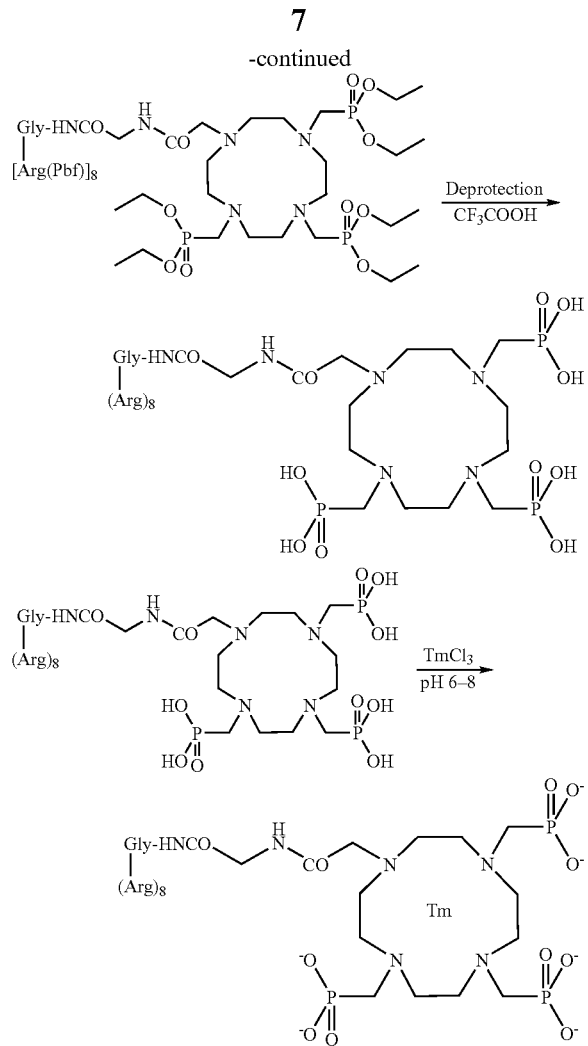

For the proposed diagnostic uses, the agents according to the invention will be formulated in appropriate compositions suitable for parenteral administration.

The diagnostic compositions according to the invention can be used to determine the chemico-physical parameters of diagnostic interest such as temperature, pH, metabolite concentration, $O_2$ and $CO_2$ partial pressures and enzyme activity in a human or animal tissue or body by means of the CEST method. For this purpose, the preferable diagnostic composition should contain two magnetically different sets of mobile protons, whose transfer effect should preferably be different towards the chemico-physical parameter of interest. In this way, by using a ratiometric method (already described in WO 00/66180), it is possible to determine the diagnostic parameter independently of the local concentration of the diagnostic composition.

Another preferred embodiment relates to the possibility of using such systems to obtain information about endothelial permeability. For this purpose, conventional diagnostic agents (namely agents on $T_1$ or $T_2$ of water protons) (Min-Ying S. et al, Magn. Res. Med. 1998, 39, 259-269) are currently used with the DCE-MRI (DCE=Dynamic Contrast Enhanced) technique. The method involves the administration of diagnostic agents of different dimensions (as such, or after interaction with macromolecules like HSA) to evaluate the permeability of the capillaries. The quantitative evaluation of capillary permeability is carried out with a kinetic study which requires successive use of the different diagnostic agents. Using the CEST procedure, however, the extravasation of each SR unit (or each SH unit) can be evaluated, as the contrast can be "stimulated" by selective irradiation of the signals of the diagnostic system. On this basis, SR units of different sizes able to shift the signal of the mobile protons of substrate SH differently (e.g. by changing the paramagnetic metal) can be used. Identification of the species which pass through the endothelium allows the kinetic study to be carried out after a single administration.

Alternatively, the same objective can be achieved by using the same SR unit and modulating the size and type of interacting substrate in order to vary the resonance frequency of its mobile protons. A similar result can be obtained by using compartmentalised systems with different dimensions wherein the diagnostic agent that passes through the endothelium can easily be identified with a suitable formulation of the solution contained in the chosen system (liposome, nanosphere, etc.).

The compositions preferably comprise an adduct according to the invention in molar concentrations of between about 0.001 and 1.0 M, in admixture with a suitable vehicle.

The compositions according to the invention can be suitably administered intravascularly (e.g. by the intravenous, intra-arterial or intraventricular route) or by the intrathecal, intraperitoneal, intralymphatic, intracavitary, oral or enteral route.

Preferred forms are sterile aqueous solutions or suspensions, ready for use or in the form of lyophilisate to be reconstituted with sterile solvent immediately before use. Depending on the specific diagnostic requirements, the dose can range between 0.01 and 0.5 mmol/kg of body weight.

The invention is described in greater detail in the examples below.

Example 1

CEST spectrum of a 0.1 mM solution of polyarginine (DP 227) at pH 6.5, 312 K, 7.05 T, irradiation time 10 s.
The spectrum (FIG. 1) indicates the intensity of the NMR signal of the bulk water according to the irradiated frequency, expressed in ppm in relation to the water.
The two CEST peaks will be observed at around 2 ppm and 4 ppm off the water, indicating the saturation transfer caused by irradiation of the guanidine protons and the amide backbone of the polymer respectively.

Example 2

Figure 2:
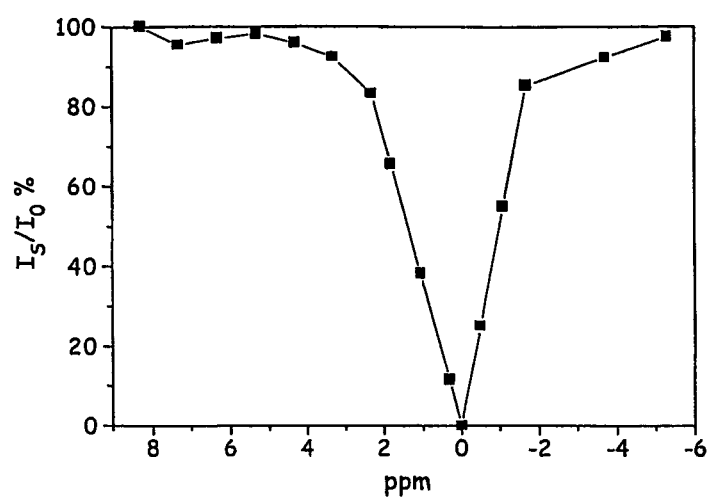
FIG. 2 demonstrates that the increase in the exchange rate of the polymer protons caused by the increase in pH leads to their coalescence with the bulk water signal.

CEST spectrum of a 0.1 mM solution of polyarginine (DP 227) at pH 7.2, 312 K, 7.05 T, irradiation time 10 s.
The spectrum (FIG. 2) demonstrates that the increase in the exchange rate of the polymer protons caused by the increase in pH leads to their coalescence with the bulk water signal.

Example 3

Figure 3:
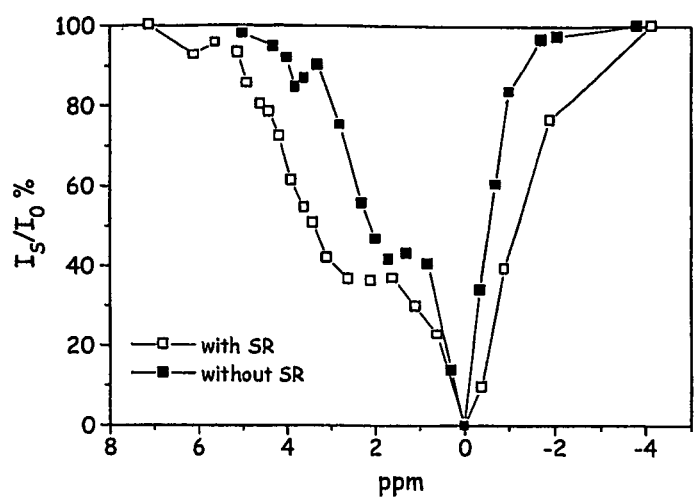
FIG. 3 shows the effect of the SR unit on the resonance frequency of the substrate.

CEST spectrum of a 0.5 mM solution of polyarginine (DP 227) in the presence of 2.5 mM of [YbDOTP]$^{4-}$ at pH 6.5, 312 K, 7.05 T, irradiation time 4 s.
The spectrum (FIG. 3) shows the effect of the SR unit on the resonance frequency of the substrate.

Example 4

CEST spectrum of a 0.5 mM solution of polyarginine (DP 227) in the presence of 2.5 mM of [YbDOTP]$^{4-}$ at pH 7.2, 312 K, 7.05 T, irradiation time 4 s.

Figure 4:
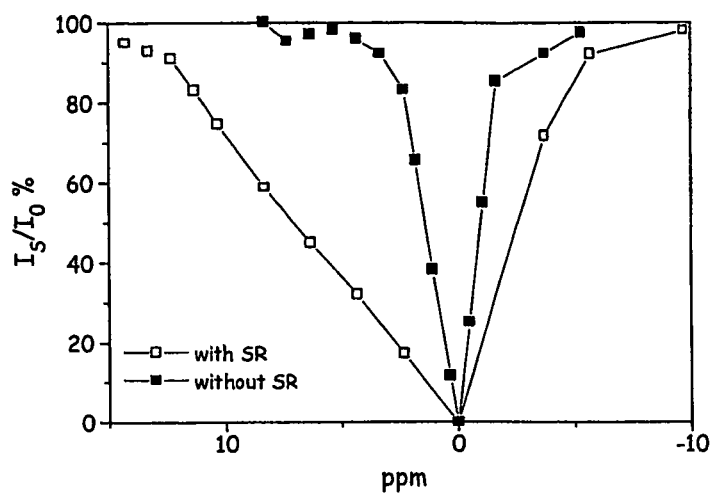
FIG. 4 demonstrates that by increasing the pH of the solution, the effect of the SR unit allows measurement of a saturation transfer for guanidine protons by irradiating in the 5-10 ppm interval off the bulk water.

The spectrum (FIG. 4) demonstrates that by increasing the pH of the solution, the effect of the SR unit allows measurement of a saturation transfer for guanidine protons by irradiating in the 5-10 ppm interval off the bulk water.

Example 5

CEST spectrum of a 0.25 mM solution of polyarginine (DP 227) in the presence of 3.5 mM of [DyDOTP]$^{4-}$ at pH 6.5, 312 K, 7.05 T, irradiation time 4 s.

Figure 5:
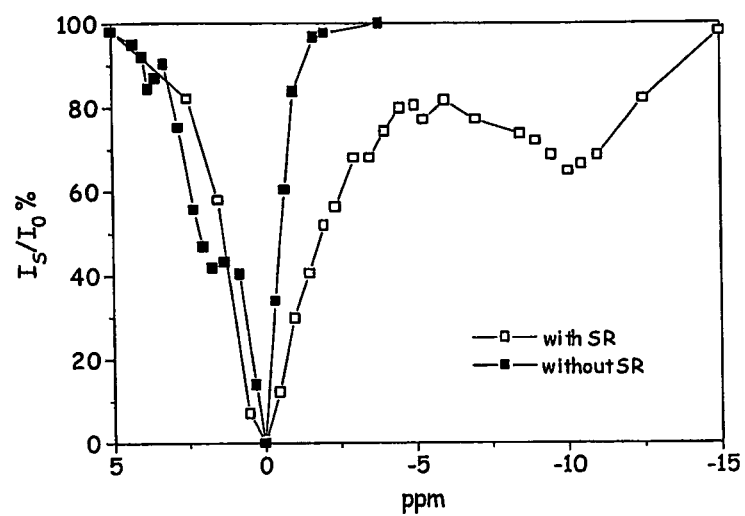
FIG. 5 illustrates that the effect of the Dy(III) ion on the resonance of the guanidine mobile protons has the opposite mathematical sign to the use of the Yb(III) ion.

The spectrum (FIG. 5) indicates that the effect of the Dy(III) ion on the resonance of the guanidine mobile protons has the opposite mathematical sign to the use of the Yb(III) ion.

Example 6

CEST spectrum of a 0.1 mM solution of polyarginine (DP 227) in the presence of 1.2 mM and 2.4 mM of [TmDOTP]$^{4-}$ at pH 7.2, 312 K, 7.05 T, irradiation time 4 s.

Figure 6:
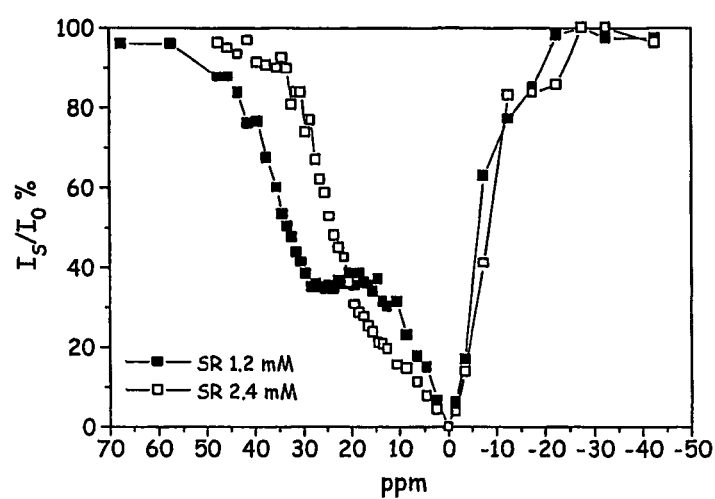
FIG. 6 indicates the marked effect of this complex on the resonance frequency of the guanidine mobile protons, whose irradiation can be carried out in the 30-40 ppm interval (2.4 mM of SR).

The spectrum (FIG. 6) indicates the marked effect of this complex on the resonance frequency of the guanidine mobile protons, whose irradiation can be carried out in the 30-40 ppm interval (2.4 mM of SR).

Example 7

Dependence of saturation transfer (ST %) on a 6.25 µM solution of polyarginine (DP 227) according to the concentration of [TmDOTP]$^{4-}$ at pH 7.2, 312 K, 7.05 T, frequency of irradiation 8400 Hz off water, irradiation time 4 s.

Figure 7:
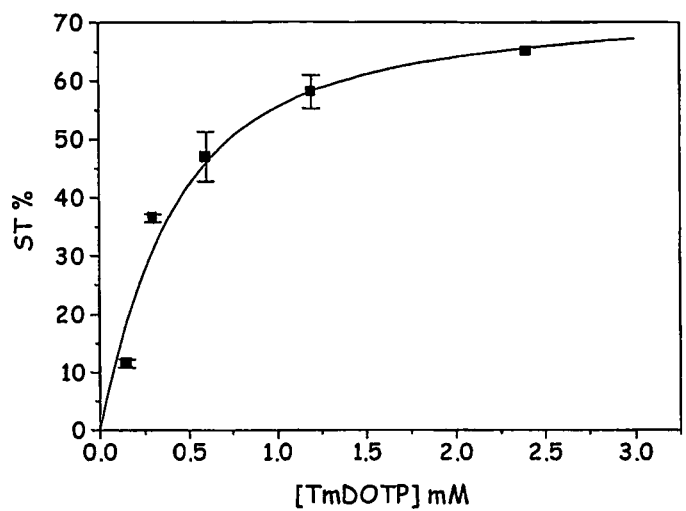
FIG. 7 shows the considerable sensitivity of this system, which can be used to measure an ST effect of 5% at an SR unit concentration of about 40 μM.

The chart (FIG. 7) shows the considerable sensitivity of this system, which can be used to measure an ST effect of 5% at an SR unit concentration of about 40 µM.

Example 8

Figure 8:
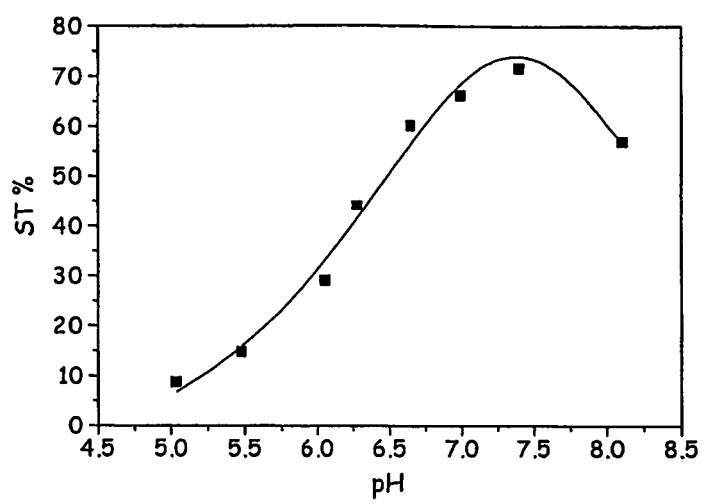
FIG. 8 shows dependence on pH of saturation transfer (ST %) of a 0.11 mM solution of polyarginine (DP 270) and 2 mM of [TmDOTP]$^{4-}$, 312 K, 7.05 T, irradiation frequency 6000 Hz off water, irradiation time 4 s.

Dependence on pH of saturation transfer (ST %) (FIG. 8) of a 0.11 mM solution of polyarginine (DP 270) and 2 mM of [TmDOTP]$^{4-}$, 312 K, 7.05 T, irradiation frequency 6000 Hz off water, irradiation time 4 s.
The effect considerably declines at an acid pH, mainly due to the reduction in exchange rate of the guanidine protons.

Example 9

Interaction between human serum albumin (HSA) and [TmDOTP]$^{4-}$ (312K, pH 7.4).

Figure 9:
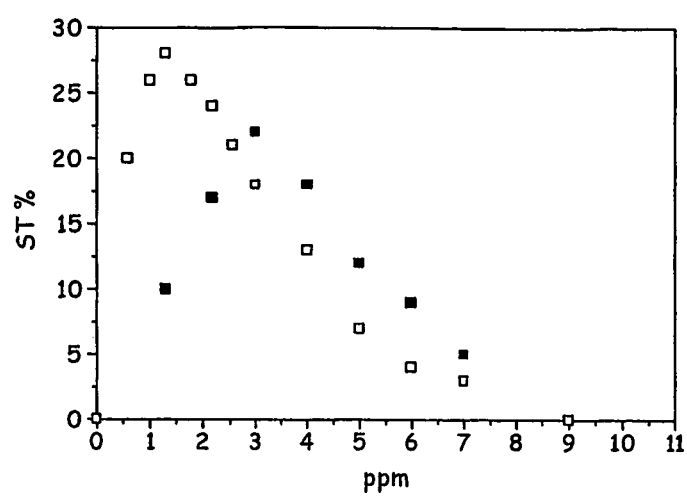
FIG. 9 shows the saturation transfer measured by irradiating the frequencies of the NMR spectrum between 1.3 ppm and 10 ppm, for a solution of HSA 1 mM alone (□) and after addition of [TmDOTP]$^{4-}$ in the amount of 3 mM (■).

FIG. 9 shows the saturation transfer measured by irradiating the frequencies of the NMR spectrum between 1.3 ppm and 10 ppm, for a solution of HSA 1 mM alone (□) and after addition of [TmDOTP]$^{4-}$ in the amount of 3 mM (■). The frequency at which the maximum transfer is observed, attributable to irradiation of the guanidine protons of the Arg protein residues, shifts by about 2 ppm.

Example 10

Interaction between [TmDOTP]$^{4-}$ and Co(en)$_3^{3+}$.

Figure 10:
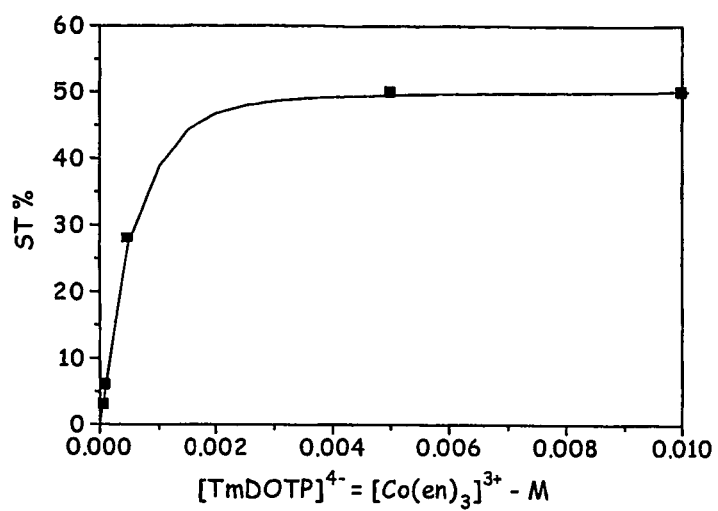
FIG. 10 illustrates the dependency of the CEST effect (ST %) according to concentration for 1:1 solutions of [TmDOTP]$^{4-}$ and Co(en)$_3$$^{3+}$, 298 K, pH 5.7, 7.05 T, frequency of irradiation 21,000 Hz off water, irradiation time 4 s.

FIG. 10 illustrates the dependency of the CEST effect (ST %) according to concentration for 1:1 solutions of [TmDOTP]$^{4-}$ and Co(en)$_3^{3+}$, 298 K, pH 5.7, 7.05 T, frequency of irradiation 21,000 Hz off water, irradiation time 4 s. Under these experimental conditions, a 5% CEST effect has been obtained at an SR unit concentration of 0.1 mM. At physiological temperature and pH, the maximum effect is only 9% due to the high exchange rate of the primary amine protons.

Example 11

Interaction between [TmDOTP]4– and Cyclen.

Figure 11:
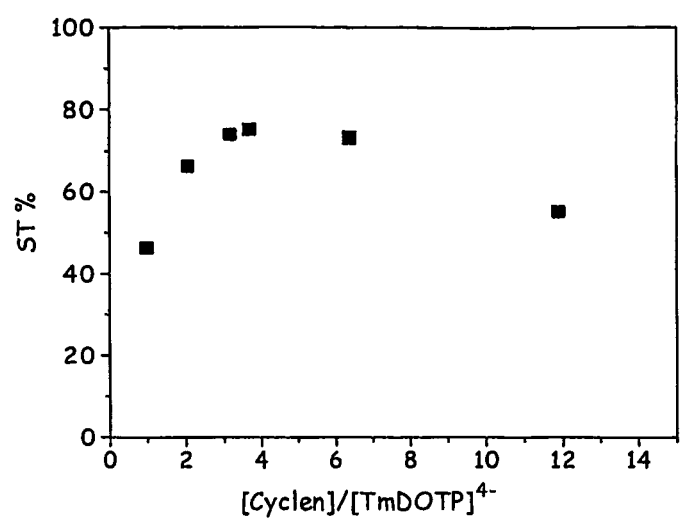
FIG. 11 indicates the dependency of the CEST effect (ST %) according to the concentration ratio between Cyclen and [TmDOTP:]$^{4-}$ for a 4 mM solution of the latter, 312 K, pH 6, 7.05 T, frequency of irradiation 21,000 Hz off water, irradiation time 4 s.

FIG. 11 indicates the dependency of the CEST effect (ST %) according to the concentration ratio between Cyclen and [TmDOTP]$^{4-}$ for a 4 mM solution of the latter, 312 K, pH 6, 7.05 T, frequency of irradiation 21,000 Hz off water, irradiation time 4 s. The maximum effect is observable for substrate/SR unit concentration ratios of about 3-4:1. At lower substrate concentrations the effect mainly declines because of the small number of protons irradiated, while at higher concentrations the effect mainly declines because of the increase in the free fraction of cyclen, with a consequent shift of the mobile proton signal to the diamagnetic area.

Example 12

Interaction between [TmDOTP]$^{4-}$ and Cyclen.

Figure 12:
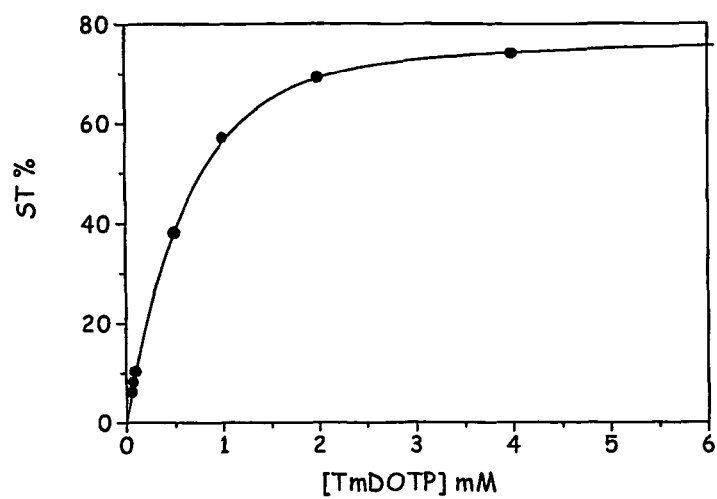
FIG. 12 illustrates the dependency of the CEST effect (ST %) on the concentration of [TmDOTP:]$^{4-}$, maintaining a [Cyclen]/[TmDOTP:]$^{4-}$ concentration ratio of 3:1, 312 K, pH 6, 7.05 T, frequency of irradiation 21,000 Hz off water, irradiation time 4 s.

FIG. 12 illustrates the dependency of the CEST effect (ST %) on the concentration of [TmDOTP]$^{4-}$, maintaining a [Cyclen]/[TmDOTP]$^{4-}$ concentration ratio of 3:1, 312 K, pH 6, 7.05 T, frequency of irradiation 21,000 Hz off water, irradiation time 4 s.

The chart shows the considerable sensitivity of this system, which can be used to measure an ST effect of 5% at an SR unit concentration of about 60 µM.

Example 13

Interaction between [TmDOTP]$^{4-}$ and Cyclen.

Figure 13:
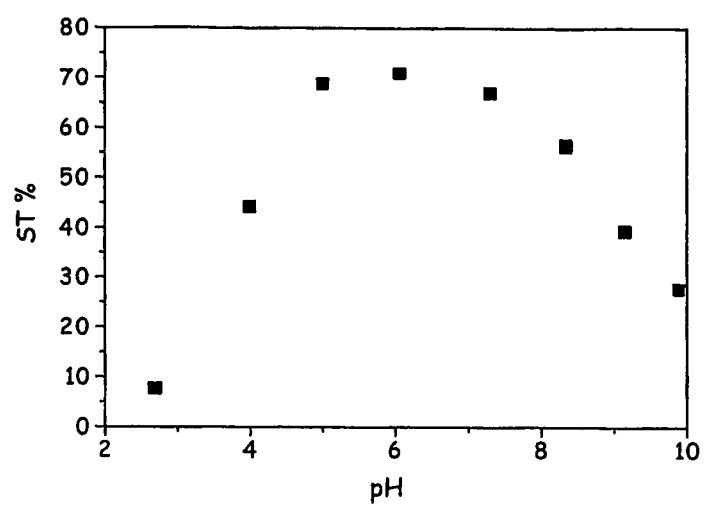
FIG. 13 shows the dependency of the CEST effect (ST %) on pH for a 3:1 solution of Cyclen (12 mM) and [TmDOTP:]$^{4-}$ (4 mM), 312 T, 7.05 T, irradiation frequency 21,000 Hz off water, irradiation time 4 s.

FIG. 13 shows the dependency of the CEST effect (ST %) on pH for a 3:1 solution of cyclen (12 mM) and [TmDOTP]$^{4-}$ (4 mM), 312 T, 7.05 T, irradiation frequency 21,000 Hz off water, irradiation time 4 s.

The transfer effect reflects the dependency of the amine proton exchange rate on the pH; in other words, it decreases when it is too slow (pH<5) or when it is too fast, approaching the condition of coalescence (pH>7).

Example 14

Figure 14:
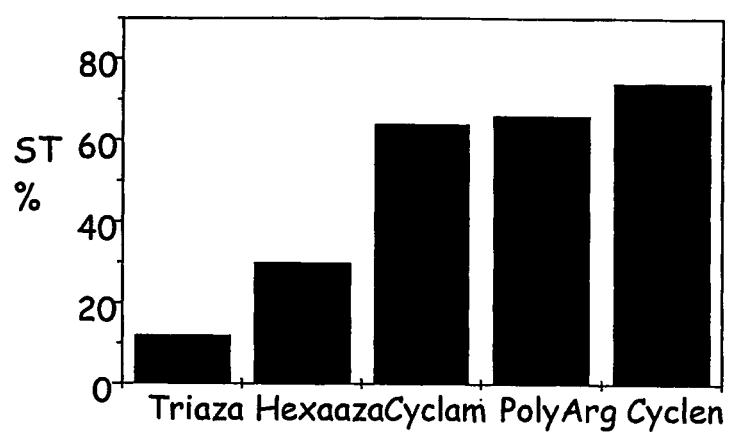
FIG. 14 compares the values of ST % for a series of substrates interacting with the SR unit [TmDOTP]$^{4-}$, 312 K, pH 7.4, 7.05 T, irradiation time 4 s.

The histogram in FIG. 14 compares the values of ST % for a series of substrates interacting with the SR unit [TmDOTP]$^{4-}$, 312 K, pH 7.4, 7.05 T, irradiation time 4 s. In all cases the concentration of [TmDOTP]$^{4-}$ is 4 mM, while that of the substrate varies according to the optimum concentration ratio previously evaluated. Triaza=1,4,7-triazacyclononane 10:1; Hexaaza=1,4,7,10,13,16-hexaazacyclooctadecane 2:1; Cyclen 3:1; Cyclam 2:1 and polyarginine 0.055:1.

The invention claimed is:
1. A method of imaging a subject comprising, administering to the subject a paramagnetic CEST agent comprising,
a substrate molecule (SH) comprising at least one mobile proton in exchange with bulk water bound by electrostatic interactions having a thermodynamic constant of association Ka greater than 10 to a paramagnetic chelate complex (SR) of a metal ion selected from the group consisting of: iron (II) (high-spin configuration), iron (III), cobalt (II), rhodium (II), copper (II), nickel (II), cerium (III), praseodymium (III), neodymium (III), dysprosium (III), erbium (III), terbium (III), holmium (III), thulium (III), ytterbium (III) and europium (III);
applying an if pulse sufficient to saturate the resonance of the at least one mobile proton shifted from the bulk water as a result of said electrostatic interaction to create a saturated magnetization that is transferred to the bulk water through chemical exchange, and imaging the subject using a CEST-based MRI procedure.

2. The method of claim 1 wherein the substrate molecule (SH) is diamagnetic and is selected from linear and cyclic polyamines, polyaminoacids, proteins, polysaccharides, polyamidoamine, peramidated polyaminoacids, dendrimers containing amide groups, polycyclodextrins, polysaccharides and alginates.

3. The method of claim 2 wherein the substrate is selected from polyarginine, albumin and cyclen.

4. The method of claim 1 in which the paramagnetic chelate is $[LnDOTP]^{4-}$ and the Ln metal ion is selected from the following: Ce(III), Pr(III), Nd(III), Eu(III), Tb(III), Dy(III), Ho(III), Er(III), Tm(III), Yb(III).

5. The method of claim 1 wherein the substrate molecule (SH) and the paramagnetic chelate complex (SR) are contained within the same compartment in biocompatible systems selected from the group consisting of liposomes, nanoparticles, microemulsions and protein cavities.

\* \* \* \* \*